United States Patent
Lendenmann et al.

(10) Patent No.: US 11,712,405 B2
(45) Date of Patent: Aug. 1, 2023

(54) METHOD FOR THE REMINERALIZATION OF TEETH

(71) Applicant: Ivoclar Vivadent AG, Schaan (LI)

(72) Inventors: Urs Lendenmann, Grabs (CH); Carlo Bolis, Igis (CH)

(73) Assignee: Ivoclar Vivadent AG, Schaan (LI)

( * ) Notice: Subject to any disclaimer, the term of this patent is extended or adjusted under 35 U.S.C. 154(b) by 4 days.

(21) Appl. No.: 16/249,464

(22) Filed: Jan. 16, 2019

(65) Prior Publication Data
US 2019/0224082 A1    Jul. 25, 2019

(30) Foreign Application Priority Data
Jan. 22, 2018   (EP) .................................. 18152850

(51) Int. Cl.
| | | |
|---|---|---|
| A61K 8/02 | (2006.01) | |
| A61K 6/17 | (2020.01) | |
| A61K 6/20 | (2020.01) | |
| A61K 8/04 | (2006.01) | |
| A61K 8/19 | (2006.01) | |
| A61K 8/24 | (2006.01) | |
| A61K 8/368 | (2006.01) | |
| A61K 8/55 | (2006.01) | |
| A61K 8/69 | (2006.01) | |
| A61Q 11/00 | (2006.01) | |

(52) U.S. Cl.
CPC .............. *A61K 8/0241* (2013.01); *A61K 6/17* (2020.01); *A61K 6/20* (2020.01); *A61K 8/04* (2013.01); *A61K 8/19* (2013.01); *A61K 8/24* (2013.01); *A61K 8/368* (2013.01); *A61K 8/55* (2013.01); *A61K 8/69* (2013.01); *A61Q 11/00* (2013.01); *A61K 2800/413* (2013.01)

(58) Field of Classification Search
CPC combination set(s) only.
See application file for complete search history.

(56) References Cited

U.S. PATENT DOCUMENTS

| | | | |
|---|---|---|---|
| 2,802,268 A | 8/1957 | Knappwost | |
| 4,397,837 A | 8/1983 | Raaf et al. | |
| 4,556,561 A | 12/1985 | Brown et al. | |
| 5,858,333 A | 1/1999 | Winston et al. | |
| 5,895,641 A | 4/1999 | Usen et al. | |
| 7,883,689 B2 * | 2/2011 | Busch | A61K 8/731 424/602 |
| 8,834,850 B2 * | 9/2014 | Busch | A61K 6/17 424/49 |
| 9,717,661 B2 * | 8/2017 | Fischer | A61K 8/463 |
| 2003/0165440 A1 * | 9/2003 | Roth | A61K 6/887 424/50 |
| 2003/0219388 A1 * | 11/2003 | Kropf | A61K 6/20 424/50 |

FOREIGN PATENT DOCUMENTS

| | | |
|---|---|---|
| DE | 10223157 C1 | 10/2003 |
| DE | 102015102156 A1 | 8/2016 |
| DE | 102016204106 A1 | 9/2017 |
| EP | 0831764 A1 | 4/1998 |
| EP | 1645263 A1 | 4/2006 |
| EP | 2676938 A1 | 12/2013 |
| RU | 2297232 * | 4/2007 |
| WO | 97/25967 A1 | 7/1997 |
| WO | 98/43602 A1 | 10/1998 |
| WO | 02/20696 A1 | 3/2002 |
| WO | 2008/068149 A1 | 6/2008 |
| WO | 2012/145619 A1 | 10/2012 |
| WO | 2014/151244 A1 | 9/2014 |

OTHER PUBLICATIONS

Walsh, Laurence J., "Contemporary technologies for remineralization therapies: A review", International Dentistry SA, vol. 11, No. 6, pp. 6-16. (Year: 2009).*

Lingström, P., et al., Comparison of Three Different Methods for Measurement of Plaque-pH in Humans after Consumption of Soft Bread and Potato Chips, J Dent Res, May 1993, vol. pp. 865-870.

Arends, J., and Christoffersen, J., The Nature of Early Caries Lesions in Enamel, Invited Review Article, J Dent Res, Jan. 1986, vol. 65, pp. 2-11.

Johansson, B., Remineralization of Slightly Etched Enamel, J Dent Res, 1965, vol. 44, pp. 64-70.

Feagin, F., et al., The Characterization of Enamel Surface Demineralization, Remineralization, and Associated Hardness Changes in Human and Bovine Material, Arch Oral Biol, 1969, vol. 14, pp. 1407-1417.

Gelhard, T.B.F.M, and Arends, J., In vivo remineralization of artificial subsurface lesions in human enamel. I., J Biol Buccale, 1984, vol. 12, pp. 49-57.

Gao, S.S, et al., Caries remineralisation and arresting effect in children by professionally applied fluoride treatment—a systematic review, BMC Oral Health, 2016, vol. 16, No. 12, pp. 1-9.

Souza, B.M., et al., Effect of an Experimental Paste with Hydroxyapatite Nanoparticles and Fluoride on Dental Demineralisation and Remineralisation in situ, Caries Research, Aug. 13, 2015, vol. 49, pp. 499-507.

* cited by examiner

*Primary Examiner* — Lezah Roberts
(74) *Attorney, Agent, or Firm* — Ann M. Knab; Thad McMurray

(57) ABSTRACT

Composition for use in the remineralization of teeth, which comprises a fluoride-containing component and a calcium-containing component, wherein the calcium-containing component contains a nanoparticulate calcium salt and the composition is designed for the successive application of the fluoride-containing component and the calcium-containing component to the tooth surface, wherein the fluoride-containing component is applied to the tooth before the calcium-containing component.

15 Claims, 11 Drawing Sheets

METHOD FOR THE REMINERALIZATION OF TEETH

CROSS-REFERENCE TO RELATED APPLICATIONS

This application claims priority to European patent application No. 18152850.6 filed on Jan. 22, 2018, the disclosure of which is incorporated herein by reference in its entirety.

FIELD OF THE INVENTION

The present invention relates to methods and compositions for the remineralization of teeth. A solution of a fluoride component is first applied to the teeth and then a sol or a colloid of a nano-calcium component is applied. This then leads to a rapid remineralization of hard tooth tissue.

BACKGROUND

Dental caries begins when acid removes minerals from the hydroxyapatite portion of the hard tooth tissue. This reduces the density of the mineral and increases the permeability of the tooth structure to liquids and ions. The acid can directly reach the teeth through nourishment, above all acidic drinks. More important, however, are carbohydrates, above all saccharose, which are fermented from biofilms on the teeth to form organic acids, above all lactic acid. The pH in the biofilm on the teeth can be lowered to approx. 4-5 within a few minutes (Lingstrom et al., 1993, J Dent Res, 72:865-870). If there is an undersaturation in relation to the solubility of hydroxyapatite in the saliva, then decalcifications form first as caries precursors (initial caries). These are recognizable macroscopically as white spots (Arends & Christoffersen, 1986, J Dent Res, 65:2-11). Unless the initial caries lesion has advanced so far that a hole forms, it can be remineralized.

Although the possibility of remineralizing enamel test pieces was already proven in the laboratory before 1970 (Johansson, 1965, J Dent Res, 44:64-70; Feagin et al., 1969, Arch Oral Biol, 14:1407-1417), today there are no products which remineralize better than fluorides in a clinically detectable and predictable manner. In fact, however, it was already described many years ago that in vivo remineralization proceeds much more slowly than in the laboratory (Gelhard & Arends, 1984, J Biol Buccale, 12:49-57).

Until now, in the prevention of caries, above all good oral hygiene and the topical application of fluoride to the teeth have proved to be successful. Fluoride reduces the solubility of hydroxyapatite. Regular application of fluoride to teeth also leads to remineralization (Gao et al. 2016, BMC Oral Health, 16:12). However, this requires a great deal of time and success is unpredictable. Methods for remineralization which lead to substantial remineralization in a short time therefore amount to a new treatment possibility in dental medicine.

WO 2012/145619 A1 describes the synthesis of calcium fluoride, dicalcium phosphate, hydroxyapatite and fluorapatite nanoparticles. These are to be suitable for the treatment of hypersensitivity of teeth. For this, the teeth are treated with a suspension or a gel which contains one or more of these nanoparticulate substances. The nanoparticles are to penetrate into the dentinal tubules and at least partially seal them.

DE 10 2015 102 156 A1 describes a method for providing a zinc and/or alkaline earth metal-rare earth metal fluoride sol solution. The sol is to be suitable for the prevention or treatment of carious lesions and can be integrated in filling materials.

U.S. Pat. No. 4,397,837, which is hereby incorporated by reference, describes a method for the remineralization of teeth in which a solution of a water-soluble calcium salt and a solution of a water-soluble phosphate, which can contain fluoride, are brought into contact with the teeth at the same time or one after the other. The substances are to penetrate into the demineralized tooth and form a precipitate there.

U.S. Pat. No. 4,556,561, which is hereby incorporated by reference, describes compositions and methods for the topical fluoridation and remineralization of dental tissue. For this, a nonaqueous dispersion is used which contains hydroxyapatite and calcium dihydrogen phosphate dihydrate or calcium dihydrogen phosphate and which is saturated with fluorapatite or calcium fluoride. A further component which contains a fluoride, such as acidulated phosphate fluoride, tin fluoride, sodium fluoride or titanium tetrafluoride, is preferably applied.

U.S. Pat. No. 5,895,641, which is hereby incorporated by reference, discloses a method for the remineralization of teeth. First, a component which contains 0.05-15 wt.-% calcium chloride or calcium nitrate is metered out. Then a second component which contains 0.5-15 wt.-% of a soluble phosphate salt and 0.01-5.0 wt.-% of a soluble fluoride salt is metered out. Then the components are mixed with water or saliva, with the result that a pH between 4.5 and 10 sets in. Immediately afterwards, the components are applied to the tooth.

U.S. Pat. No. 5,858,333, which is hereby incorporated by reference, describes a 2-component oral hygiene product which is to mineralize initial lesions in teeth or exposed dentinal tubules. The first cationic component contains a water-soluble calcium salt in a pharmaceutically acceptable carrier material. The second anionic component contains a water-soluble phosphate salt in a pharmaceutically acceptable carrier material. The carrier material of one of the components is aqueous and that of the other is not aqueous, but rather hydrophilic. The two components are mixed together before application.

WO 98/43602 discloses two-component agents for the remineralization of teeth, which contain a cationic component A and an anionic component B. The cationic component A contains a completely or partially water-soluble calcium compound and the anionic component B contains a water-soluble fluoride compound. The components are mixed together before being applied to the teeth. The calcium-containing component additionally contains a water-soluble magnesium compound, which is to delay the reaction between the calcium compound and the fluoride compound after the components have been mixed.

DE 102 23 157 C1 discloses a method for repairing defects on tooth material. For this, a gelatin gel which contains phosphate ions and optionally fluoride ions and a so-called protective gel which is free of phosphate ions are applied to the tooth sequentially. Then the tooth is treated with a medium containing calcium ions. For this, the tooth is stored in a calcium chloride solution for several days in the embodiment examples. The method is to cause the growth of an apatite layer on the tooth surface.

EP 1 645 263 A1 describes an oral hygiene product which comprises a fluoride-containing composition A and a calcium-containing composition B. Component A additionally contains an inorganic phosphoric acid or a salt thereof. Component B contains the calcium salt of an organic acid with a pK value of from 3 to 11. The two components are applied to the tooth one after the other, where they are to react with each other, forming calcium fluoride or calcium phosphate. The absorption of calcium fluoride and calcium phosphate into the tooth is to be improved hereby.

WO 2008/068149 A1 describes an oral hygiene product which comprises a first composition, which contains an insoluble calcium salt, and a second composition, which contains a source of phosphate ions. The first composition preferably contains neither phosphate nor fluoride ions. The insoluble calcium salt is to be converted to hydroxyapatite in situ on the tooth surface by the phosphate ions.

U.S. Pat. No. 2,802,268, which is hereby incorporated by reference, describes a method for sealing fissures between tooth and filling in which first a soluble silicofluoride such as $MgSiF_6$ is introduced into the gap and then the precipitation of silicon dioxide, magnesium fluoride and calcium fluoride is brought about by an alkaline liquid such as e.g. a calcium hydroxide suspension.

EP 2 676 938 A1 discloses a method for preparing a calcium fluoride sol in which a calcium compound is provided in a nonaqueous solvent with a nonaqueous hydrogen fluoride solution. The salts of organic acids, such as e.g. calcium acetate or calcium lactate, are preferably used as calcium compound. Preferred nonaqueous solvents are alcohols such as e.g. methanol or ethanol. The sols are to be suitable for the production of anti-reflective coatings on glass.

WO 02/20696 A1 describes the synthesis of metal salt nanoparticles. The nanoparticles can have fluorescent properties. In this method a metal salt is dispersed or dissolved, as a cation source together with an anion source and a component controlling crystal growth, in an organic solvent and then kept at a predefined temperature. Calcium salts, among others, are suitable as metal salts.

SUMMARY

The object of the invention is to provide compositions and methods which are suitable for the remineralization of teeth, for the treatment of initial caries lesions, for caries protection and for the prevention and treatment of dental erosions.

The object is achieved by a method in which first a solution of a fluoride-containing component and then a sol of a calcium-containing component in a volatile solvent are applied to the tooth surface to be treated. According to a preferred embodiment, before the fluoride component is applied, the tooth surface is subjected to an optional pretreatment, for example an acid treatment and/or dental cleaning.

BRIEF DESCRIPTION OF THE DRAWINGS

Further advantages, details and features result from the following description of several examples of profiles in accordance with the invention, while reference is made to the drawings, wherein.

DETAILED DESCRIPTION

Figure 1:
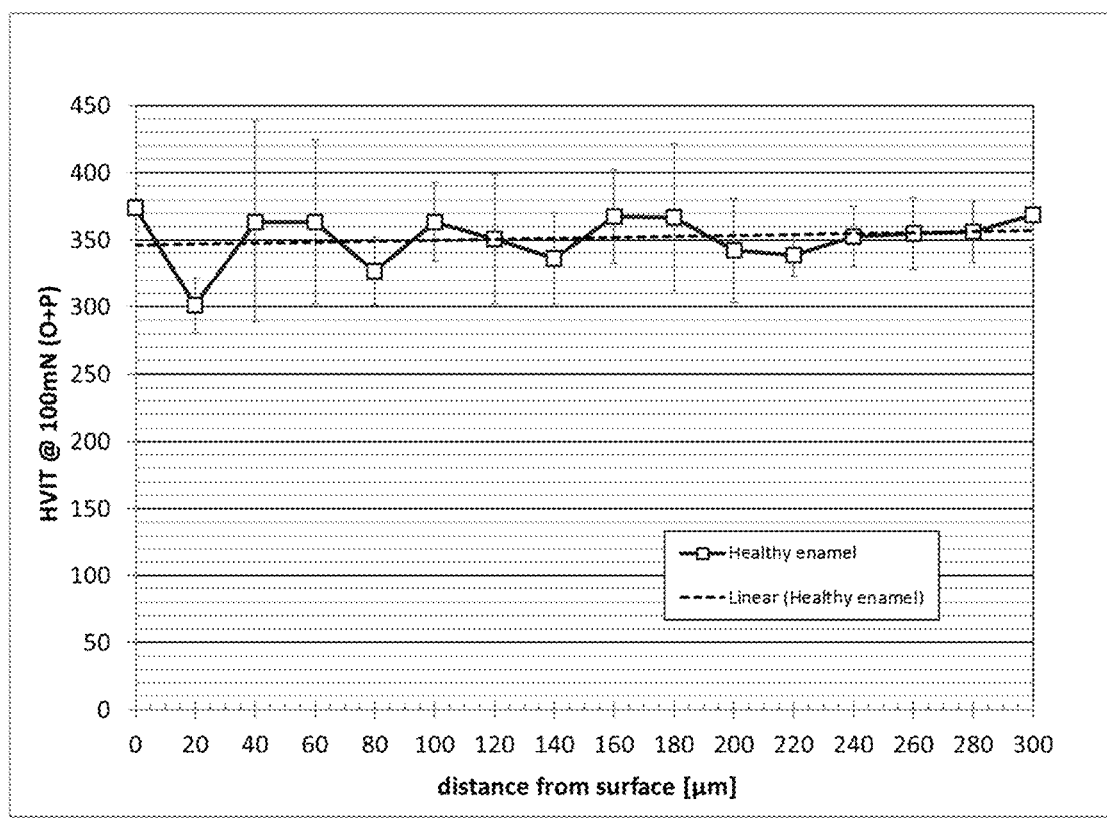
FIG. 1 shows the hardness profile of an untreated tooth. The hardness of the tooth at the surface (distance=0 µm) corresponds to the hardness in deeper regions (distance=300 µm).

The invention relates to a composition and a method for the remineralization of teeth, in particular for the treatment of initial caries lesions, for example of fissures, smooth surfaces, interdental surfaces and dental crevices, for caries protection on selected tooth surfaces, and for the prevention and treatment of dental erosions.

The method according to the invention comprises the following steps:
(i) optional pre-treatment of the tooth,
(ii) application of a fluoride component and
(iii) application of a nano-calcium component.

The nanoparticulate calcium component forms a solid layer after being applied to the tooth surface.

The fluoride-containing components and the calcium-containing component are present in a spatially separated form.

I. Optional Pre-Treatment of the Tooth

The tooth areas to be treated are preferably cleaned before the actual treatment. In the process tartar (calculus) and other deposits on the teeth are removed. A professional dental cleaning is particularly preferably carried out.

As a thin film of debris, the so-called smear layer, can remain on the tooth after a (professional) dental cleaning completed by a polishing, it is preferred to etch the tooth areas to be treated slightly, so that the subsequent fluoride component can penetrate deep into the dental enamel. For this, dots of an etchant are applied to the regions in question, in particular the demineralized initial lesions visible as white spots, and left there for a short time. This is followed by rinsing. The exposure time of the acid is not very critical. It should be long enough to dissolve the smear layer, but not so long that the dental enamel is unnecessarily weakened. Times of between 1 s and 1000 seconds, preferably 5 s-120 s, particularly preferably 5 s-60 s, are preferred according to the invention.

Aqueous solutions of phosphoric acid, hydrochloric acid, nitric acid, sulphuric acid, lactic acid, acetic acid, formic acid, citric acid, ethylenediaminetetraacetic acid, etc. come into consideration as acids for the etching. Phosphoric acid and lactic acid are preferred, phosphoric acid is particularly preferred, preferably 37% phosphoric acid.

So that these acid solutions can be applied in dots precisely, they preferably contain a thickener. Such etchants are known per se from dental adhesive technology and have been thoroughly described. 37% phosphoric acid etching gel, such as e.g. the commercially available gel called Total Etch from Ivoclar Vivadent AG, is preferred.

The etchant is rinsed off with water after the desired exposure time and the tooth is then dried, preferably with an air jet, but other methods are also suitable.

II. Application of Fluoride Component

After the cleaning and/or the acid treatment, the fluoride component is applied to the tooth.

It is recommended, in the context of a comprehensive fluoridation of the teeth, to apply the fluoride component to the entire natural set of teeth after a dental cleaning. However, the fluoride component can also be easily applied only to the sites to be treated, particularly when no professional dental cleaning has been carried out beforehand. It is important for the success of the method, however, that fluoride solution has also been applied to all surfaces to which the nano-calcium component is then applied.

A composition which contains one or more of the following fluoride compounds is preferably used as fluoride component: sodium fluoride, potassium fluoride, ammonium fluoride, ammonium bifluoride, sodium monofluorophosphate, potassium monofluorophosphate, salts of tetra- or hexafluoro anions such as e.g. ammonium hexafluorosilicate, magnesium hexafluorosilicate, potassium hexafluorophosphate, ammonium hexafluorotitanate, ammonium tetrafluorotitanate, ammonium hexafluoroaluminate, zirconium fluoride, tetra-n-butylammonium dihydrogen trifluoride (TBAF-3), rubidium fluoride, caesium fluoride, potassium bifluoride ($KHF_2$), silver(I) fluoride (AgF), tin(II) fluoride ($SnF_2$), olaflur and dectaflur. The following are particularly preferred: ammonium fluoride, ammonium bifluoride, potassium fluoride, tetra-n-butylammonium dihydrogen trifluoride.

The fluoride compound(s) is/are preferably used in the form of a solution. Substances or substance mixtures which can at least partially and preferably completely dissolve the fluoride compound are suitable as solvents.

Preferred solvents are water, ethanol, isopropanol, acetone, methanol and propylene glycol or mixtures thereof. Water, ethanol, isopropanol and acetone or mixtures thereof are particularly preferred. Acetone or mixtures of acetone with water, ethanol or isopropanol are particularly preferred in particular for tetra-n-butylammonium dihydrogen trifluoride.

Solutions which contain more than 1500 ppm, preferably more than 5000 ppm, fluoride (relative to the fluoride anion) in dissolved form are preferred. The maximum concentration depends on the choice of the solvent and the fluorine salt. It preferably lies below 20 wt.-%, particularly preferably below 10 wt.-%.

Optionally, this fluoride solution can also contain acids, so that deposits, which could prevent the penetration of the subsequent components, are removed. In particular phosphoric acid, hydrochloric acid, nitric acid, sulphuric acid, lactic acid, acetic acid, formic acid, citric acid, ethylenediaminetetraacetic acid, etc. come into consideration as acids. The fluoride solution preferably contains no phosphate.

After the fluoride solution has been applied, excess fluoride solution should be removed as far as possible. This can be effected by blowing with air, or using an aspirator or a swab. If there is no excess fluoride solution on the teeth, then it is possible to move on immediately. The teeth can optionally be dried after the fluoride solution has been applied.

III. Application of Nano-Calcium Component

After the fluoride component, the nano-calcium component is applied. This can again be applied over the whole surface of the entire set of teeth or only to the areas to be treated. After application, the calcium component forms a layer which completely or partially covers the tooth. The layer formation is effected for example when the solvent of the calcium component evaporates. Here, the nano-calcium particles thicken to form a layer. The layer formation is preferably accelerated by the active drying of the calcium component. The formation of a layer can, however, also be brought about in another way, for example by the addition of a gelling agent to the calcium component. The layer formation can also be effected by spontaneous aggregation of the particles, for example when the sol comes into contact with water or saliva.

The calcium component contains a calcium salt, preferably calcium fluoride, calcium carbonate, calcium sulphate, calcium silicate, calcium oxide or calcium hydroxide. Calcium fluoride, calcium carbonate, calcium sulphate and calcium silicate, quite particularly calcium carbonate and in particular calcium fluoride are particularly preferred. According to the invention the calcium salt is present in nanoparticulate form. Nanoparticles with a particle size of <100 nm, particularly preferably <40 nm and quite particularly preferably <30 nm, are preferred. The particle size preferably lies in a range of from 1 to 100 nm, particularly preferably 1 to 40 nm and quite particularly preferably 1 to 30 nm.

In all cases, unless expressly stated otherwise, the particle size is the average particle diameter (number average) measured using dynamic light scattering (DLS), preferably using a Malvern ZetaSizer.

The calcium component preferably contains no phosphate, in particular no calcium phosphate.

The nanoparticulate calcium salt is present as a sol in a volatile suspending agent. In particular orally acceptable solvents which evaporate on their own within a short time under normal ambient conditions or under oral conditions or can be dried up with the aid of an air jet come into consideration as suspending agents for the calcium particles. Preferred suspending agents are alcohols, esters, ethers, ketones, alkanes, alkenes, water or mixtures thereof, in particular ethanol, methanol, n-propanol, i-propanol, n-butanol, sec-butanol, isoamyl alcohol, acetone, water, acetonitrile, ethyl acetate, methoxy propanol, dibutyl ether, dioxane, methyl ethyl ketone, heptane, hexane or dimethylformamide. Ethanol, acetone, isopropanol, water and mixtures thereof are particularly preferred. Organic solvents or mixtures of organic solvents and water are preferred, anhydrous solvents are particularly preferred.

An important aspect of the invention is that the calcium component contains nanoparticulate particles of a calcium salt. The calcium salt and also the type and quantity of the suspending agent are therefore chosen such that the particles do not dissolve in the solvent. They have to be present in particulate form at least during application. The nanoparticulate calcium salt and the suspending agent can be present in separated form. In this case, the calcium salt is dispersed in the suspending agent before application. Ready-made suspensions (sols) of the calcium particle or calcium particles are preferred.

Suspensions which have a pH of less than 11.0 and preferably less than 10 are preferred according to the invention. In the case of anhydrous suspensions, the suspension is mixed with water in a ratio of 1:1 to determine the pH. The pH preferably lies in a range of from 4.4 to 11, particularly preferably 5 to 10 and quite particularly preferably 6 to 10.

The proportion of the calcium salt in the sol or colloid can lie between 0.0001 and 99.9999 wt.-%. Proportions of from 0.1 wt.-% to 40 wt.-%, particularly preferably 1 wt.-% to 30 wt.-%, quite particularly preferably 5 wt.-% to 25 wt.-% and in particular 6 wt.-% to 12 wt.-%, are preferred.

However, the proportion should also not be too high, so that the sol or colloid remains thin enough to be able to be applied to the tooth using a brush or small brush.

After the sol has been applied to the tooth surface, the nanoparticles form a solid layer on the tooth surface. The layer formation is preferably effected by evaporation of the solvent, wherein the drying can be actively accelerated, for example by blowing the solvent with an air jet. After the drying, the dried layer can remain on the tooth. It is worn away in the course of time, for example during tooth brushing. However, it is also possible to actively remove the layer after the treatment.

The invention is explained in more detail below by means of figures and examples.

EMBODIMENT EXAMPLES

Example 1

Determination of the remineralization potential in a caries-producing environment The remineralization potential on the tooth was tested in a model with a chemically produced initial lesion in bovine enamel. For this, bovine teeth were embedded in resin, and the enamel was exposed and polished with SiC sandpaper, accompanied by water cooling. An artificial lesion was produced in the enamel by storage in a demineralizing solution for 14 to 21 days at 37° C. The demineralizing solution contained 50.0 mmol/l acetic acid, 3.0 mmol/l $KH_2PO_4$, 3.0 mmol/l $CaCl_2 \cdot 2\, H_2O$, 1.0 ppm methylenediphosphonic acid as well as another 100 ppm sodium azide as preservative. The pH was set to pH 5.0 with KOH.

Half of the thus-produced lesions were covered with nail varnish, the free surface was treated using the method according to the invention. The test piece was then stored in the demineralizing solution at pH 5.0 for 7-14 days at 37° C. Each treatment was carried out on two teeth each.

After the storage, the test pieces were rinsed briefly with water, patted dry and the nail varnish was removed from the isolated half with ethanol. The surface hardness of both halves was measured using a nanoindenter. The surface of the test pieces was likewise embedded with resin, in order then to be able to saw out a disc of the tooth cross section using a diamond saw. After the cross section had been polished, three hardness profiles each of the treated and isolated sides were measured (impressions with a distance of 20 μm in each case vertically up to a depth of 300 μm, Berkovich indenter, 80 or 100 mN load, loading with 400 or 600 mN/min., 2 s holding time at $F_{max}$. The hardness profiles were generated using the Vickers hardness values calculated automatically by the device.

The hardness profile of an untreated tooth is shown in FIG. 1. It can be seen that the hardness of the tooth at the surface (distance=0 μm) is exactly as high as in deeper regions (distance=300 μm).

Figure 2:
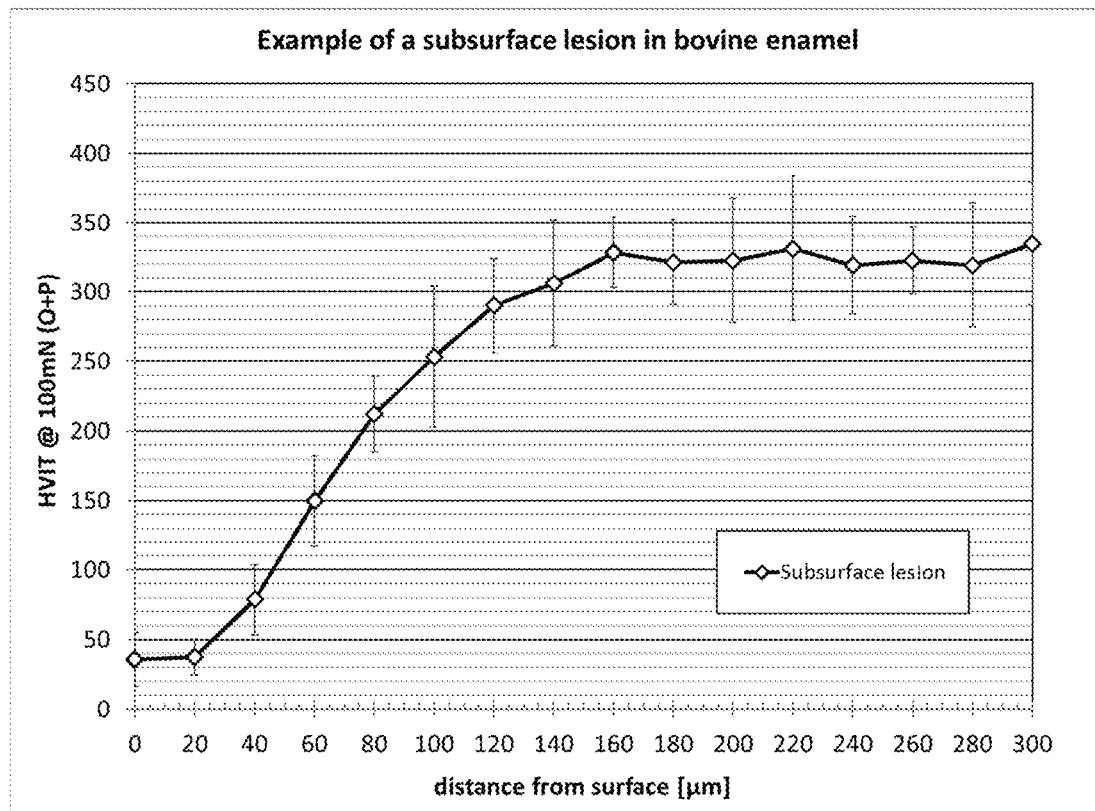
FIG. 2 shows the hardness profile of the tooth after storage in a demineralization solution. The demineralization of the tooth is associated with a clear decrease in the hardness, which reveals itself particularly at the tooth surface, which is in direct contact with the demineralization solution.

FIG. 2 shows the hardness profile of the tooth after storage in the demineralization solution. Here, the hardness at the tooth surface which was in direct contact with the demineralization solution is clearly reduced (from approx. 320 $HV_{IT}$ to approx. 40 $HV_{IT}$). The hardness profile shows that the demineralization has an effect in the chosen conditions up to a depth of approx. 160 μm measured from the tooth surface. From a depth of approx. 160 μm, the tooth has the natural hardness.

Example 2

Remineralization with Ammonium Fluoride Solution and Calcium Hydroxide Nanosol

Remineralization of an initial lesion by application of a 10% ammonium fluoride solution (5.14 wt.-% fluoride) for 5 minutes and subsequent application of a calcium hydroxide nanosol (50 g/l in ethanol, absolute grain-size range 50-250 nm; obtained from IBZ-Salzchemie GmbH & Co. KG, 09633 Halsbrücke, Germany). After the sol had dried up, the teeth were stored in the demineralizing solution for 14 days.

Figure 3:
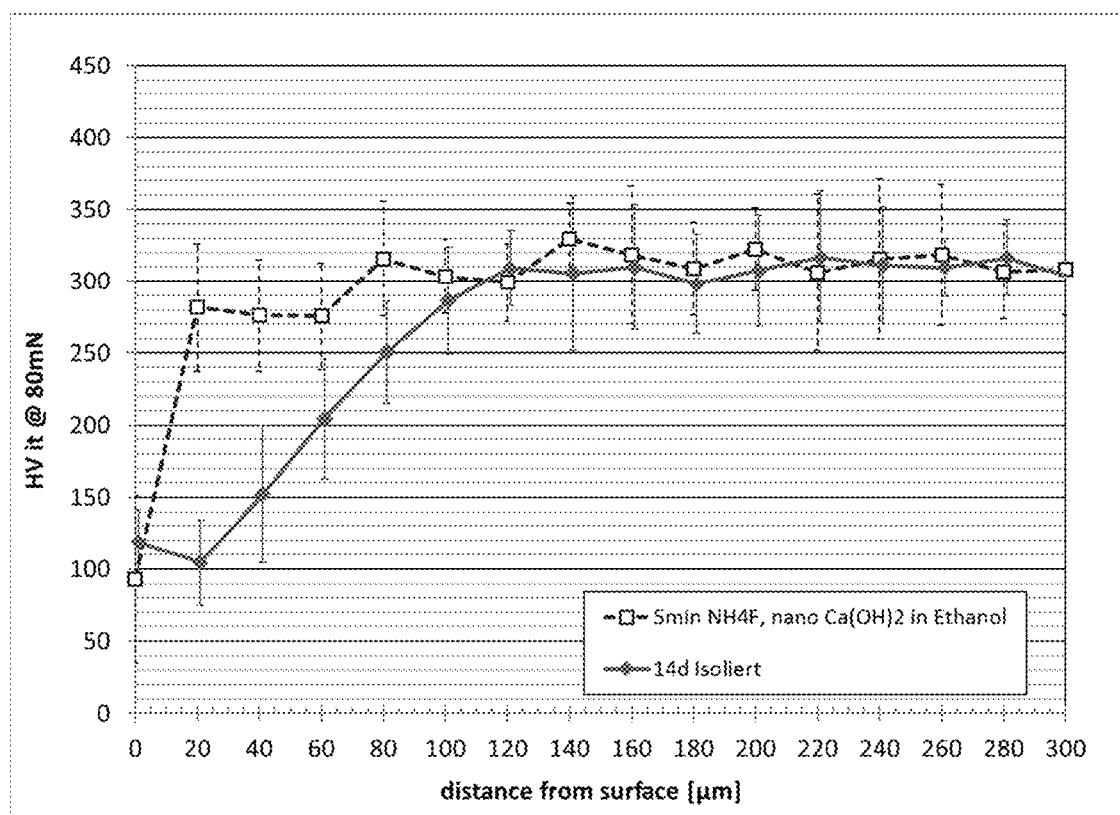
FIG. 3 shows the hardness profile of a tooth region which has been treated with a composition according to the invention (NH4F, thereafter ethanolic Ca(OH)2 nanosol) (dashed curve), compared with an untreated enamel sample (continuous curve). The composition according to the invention brings about a clear increase in the hardness in the demineralized enamel sample. The increase in hardness is to be attributed to the remineralization of the tooth.

The hardness profiles of this sample are reproduced in FIG. 3. The continuous line shows the profile of the half of the enamel samples isolated using nail varnish. The hardness of the enamel sample in the surface region is clearly reduced by the demineralization (from approx. 300 $HV_{IT}$ to approx. 100 $HV_{IT}$).

The dashed curve shows the hardness profile of the enamel sample which was treated with the composition according to the invention and then exposed to the demineralization solution again.

The treatment brought about a very clear increase in the hardness in the surface region and thus a remineralization of the tooth.

Example 3

Remineralization with Ammonium Fluoride Solution and Calcium Carbonate Nanosol (6%)

Remineralization of an initial lesion by application of a 10% ammonium fluoride solution (5.14 wt.-% fluoride) for 5 minutes and subsequent application of a calcium carbonate nanosol (6 wt.-% in ethanol, average particle diameter measured using dynamic light scattering (DLS) of approx. 70 nm; obtained from Mathym SAS, 69410 Champagne-au-Mont-d'Or, France). After the sol had dried up, the teeth were stored in the demineralizing solution for 9 days.

Figure 4:
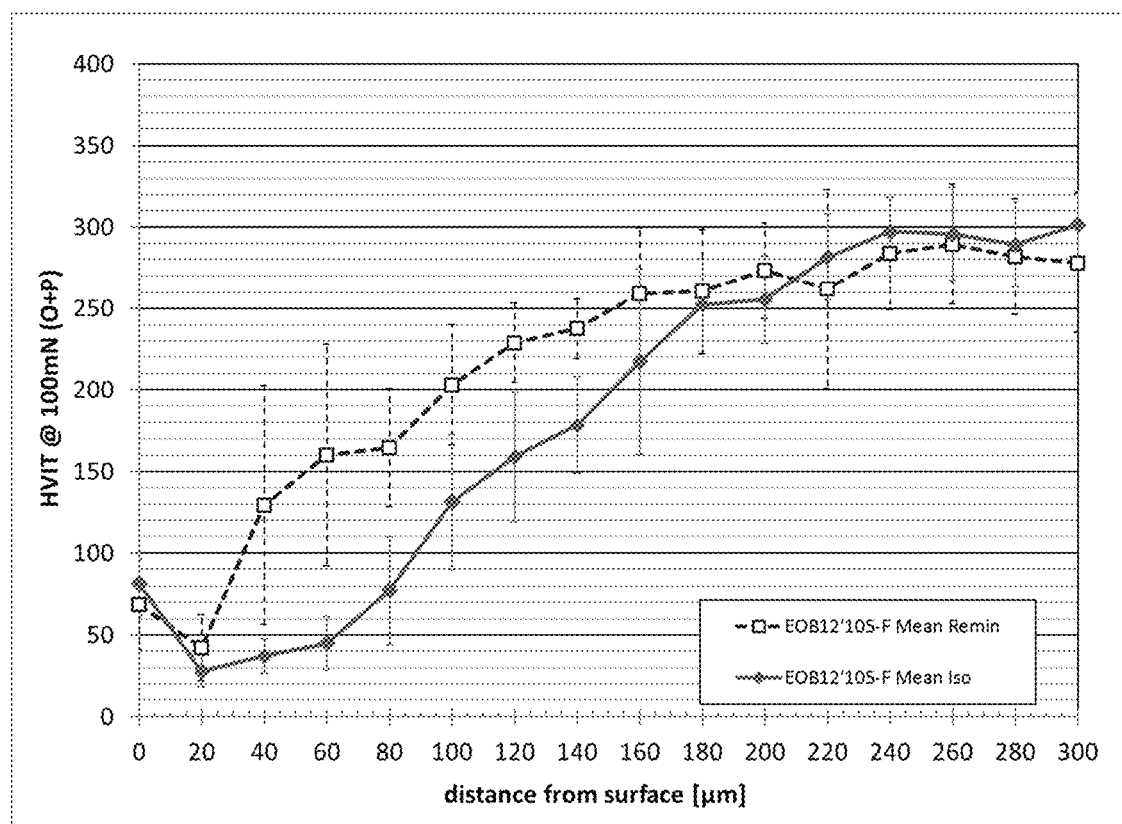
FIG. 4 shows the hardness profile of a tooth region which has been treated with a composition according to the invention (NH4F, thereafter ethanolic CaCO3 nanosol) (dashed curve), compared with an untreated enamel sample (continuous curve).

The hardness profiles in FIG. 4 show that the treatment with the solution according to the invention brings about a clear increase in hardness.

Example 4

Remineralization with Ammonium Fluoride Solution/Calcium Fluoride Nanosol (10.6%, 7 days)

Remineralization of an initial lesion by application of a 10% ammonium fluoride solution (5.14 wt.-% fluoride) for 5 minutes and subsequent application of a calcium fluoride nanosol (10.6 wt.-% in ethanol, average particle diameter measured using a transmission electron microscope (TEM) of approx. 20 nm, or using DLS of approx. 30 nm; obtained from Mathym SAS, 69410 Champagne-au-Mont-d'Or, France). After the sol had dried up, the teeth were stored in the demineralizing solution for 7 days.

Figure 5:
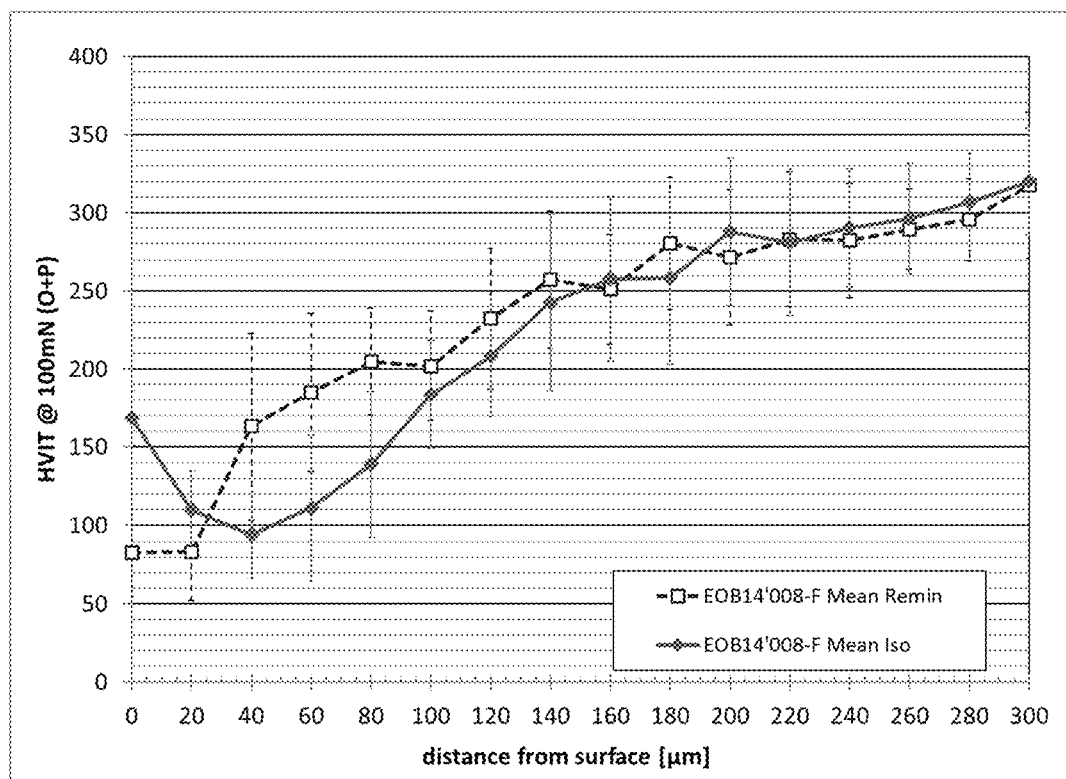
FIG. 5 shows the hardness profile of a tooth region which has been treated with a composition according to the invention (NH4F, thereafter ethanolic CaF2 nanosol) (dashed curve), compared with an untreated enamel sample (continuous curve). The samples were stored in the demineralizing solution for 7 days.

The hardness profiles of the samples are shown in FIG. 5. A clear increase in hardness can be seen in the case of the sample treated according to the invention.

Example 5

Remineralization with Ammonium Fluoride Solution/Calcium Fluoride Nanosol (10.6%, 14 days)

Remineralization of an initial lesion by application of a 10% ammonium fluoride solution (5.14 wt.-% fluoride) for 5 minutes and subsequent application of a calcium fluoride nanosol (10.6 wt.-% in ethanol, average particle diameter measured using TEM of approx. 20 nm, using DLS of approx. 30 nm; obtained from Mathym SAS, 69410 Champagne-au-Mont-d'Or, France). After the sol had dried up, the teeth were stored in the demineralizing solution for 14 days.

Figure 6:
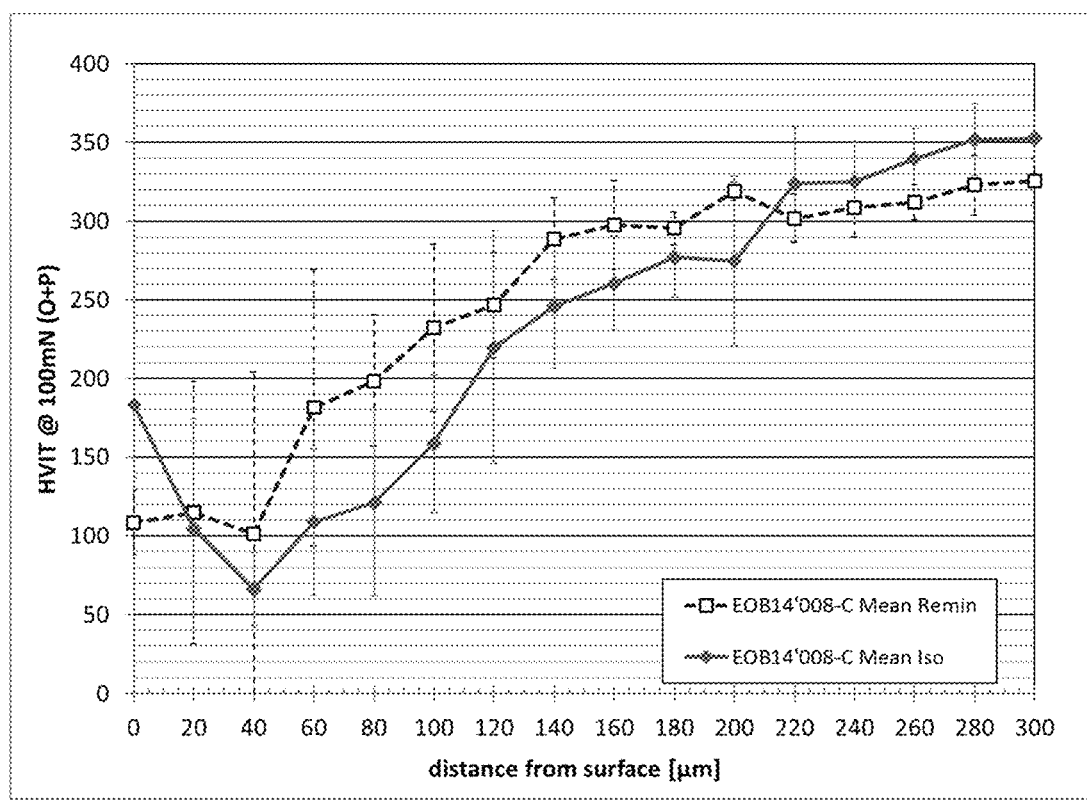
FIG. 6 shows the hardness profile of a tooth region which has been treated with a composition according to the invention (NH4F, thereafter ethanolic CaF2 nanosol) (dashed curve), compared with an untreated enamel sample (continuous curve). The samples were stored in the demineralizing solution for 14 days.

The hardness profiles in FIG. 6 provide evidence for an effective remineralization of the tooth.

Example 6

Remineralization with Ammonium Fluoride Solution and Calcium Fluoride Nanosol (6.5%)

Remineralization of an initial lesion by application of a 10% ammonium fluoride solution (5.14 wt.-% fluoride) for 5 minutes and subsequent application of a calcium fluoride nanosol (6.5 wt.-% in ethanol, average particle diameter measured using TEM of approx. 10 nm, using DLS of approx. 30 nm; obtained from Mathym SAS, 69410 Champagne-au-Mont-d'Or, France). After the sol had dried up, the teeth were stored in the demineralizing solution for 7 days.

Figure 7:
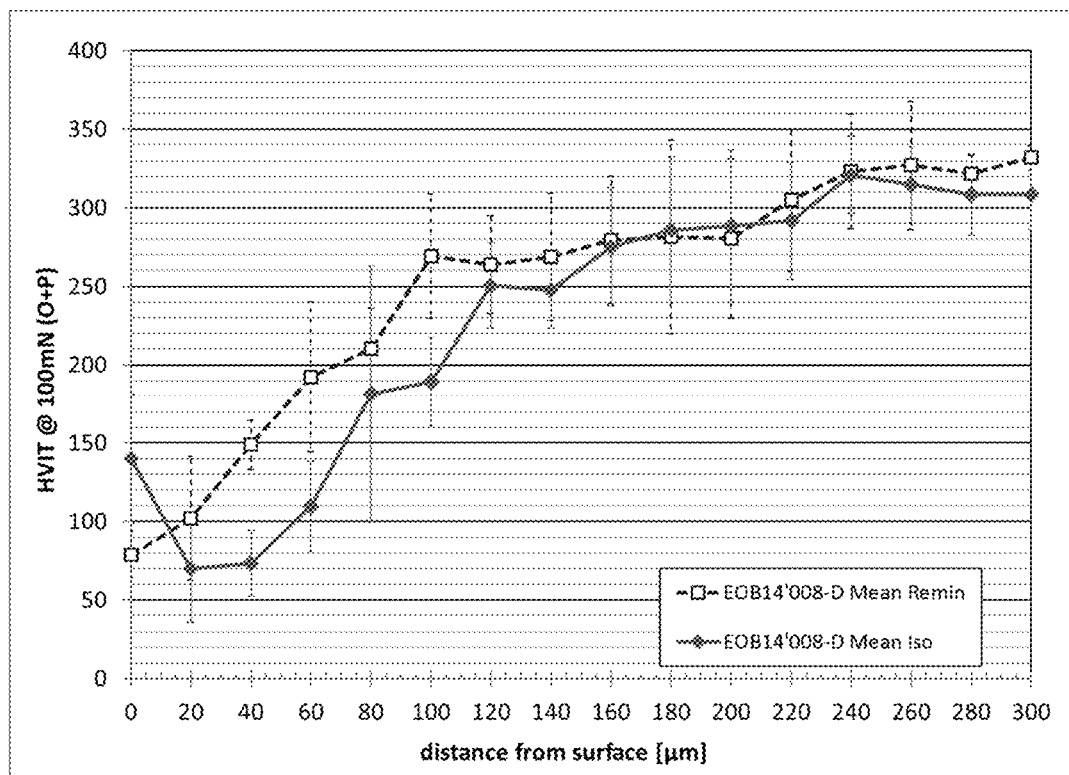
FIG. 7 shows the hardness profile of a tooth region which has been treated with a composition according to the invention (NH4F, thereafter ethanolic CaF2 nanosol) (dashed curve), compared with an untreated enamel sample (continuous curve). The samples were stored in the demineralizing solution for 7 days. The CaF2 content is smaller than in FIG. 5.

The hardness profiles of the samples are shown in FIG. 7. They provide evidence for an effective remineralization of the tooth.

Example 7

Remineralization with Ammonium Fluoride Solution and Calcium Fluoride Nanosol (7.1%)

Remineralization of an initial lesion by application of a 10% ammonium fluoride solution (5.14 wt.-% fluoride) for 5 minutes and subsequent application of a calcium fluoride nanosol (7.1 wt.-% in ethanol, average particle diameter measured using TEM of approx. 10 nm, approx. 30 nm using DLS; obtained from Mathym SAS, 69410 Champagne-au-Mont-d'Or, France). After the sol had dried up, the teeth were stored in the demineralizing solution for 14 days.

Figure 8:
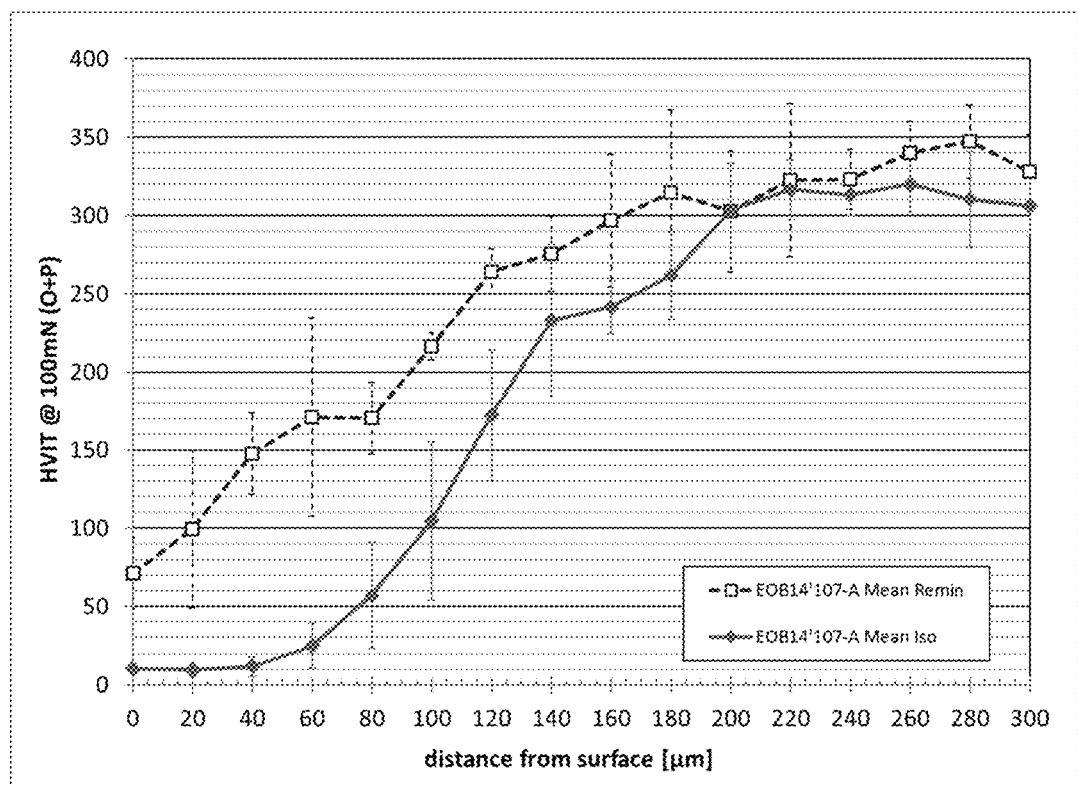
FIG. 8 shows the hardness profile of a tooth region which has been treated with a composition according to the invention (NH4F, thereafter ethanolic CaF2 nanosol) (dashed curve), compared with an untreated enamel sample (continuous curve). The samples were stored in the demineralizing solution for 14 days. The CaF2 content is smaller than in FIG. 6.

The hardness profiles in FIG. 8 show a very clear increase in the hardness after the remineralization of the tooth.

Example 8

Remineralization with Ammonium Bifluoride Solution/Calcium Fluoride Nanosol

Remineralization of an initial lesion by application of a 3.85% solution of ammonium bifluoride $NH_4HF_2$ (2.56 wt.-% fluoride) for 1 minute and subsequent application of a calcium fluoride nanosol (7.1 wt.-% in ethanol, average particle diameter measured using TEM of approx. 10 nm, approx. 30 nm using DLS; obtained from Mathym SAS, 69410 Champagne-au-Mont-d'Or, France). After the sol had dried up, the teeth were stored in the demineralizing solution for 14 days.

Figure 9:
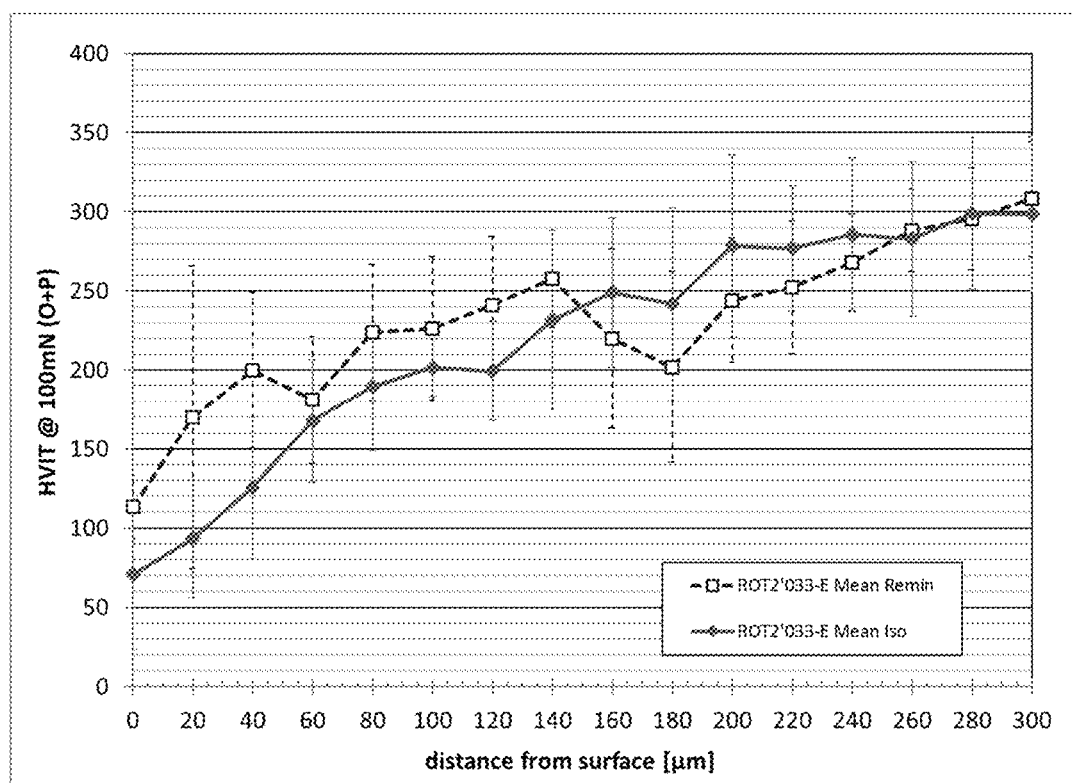
FIG. 9 shows the hardness profile of a tooth region which has been treated with a composition according to the invention (NH4HF2,thereafter ethanolic CaF2 nanosol) (dashed curve), compared with an untreated enamel sample (continuous curve).

The hardness profiles in FIG. 9 show a clear, if also slightly less pronounced than in the rest of the examples, increase in hardness after the remineralization.

Example 9

Remineralization with Tetrabutylammonium Dihydrogen Trifluoride/Calcium Fluoride Nanosol Remineralization of an initial lesion by application of a 13.58% solution of tetrabutylammonium dihydrogen trifluoride in water (2.56 wt.-% fluoride) for 1 minute and subsequent application of a calcium fluoride nanosol (7.1 wt.-% in ethanol, average particle diameter measured using TEM of approx. 10 nm, using DLS of approx. 30 nm; obtained from Mathym SAS, 69410 Champagne-au-Mont-d'Or, France). After the sol had dried up, the teeth were stored in the demineralizing solution for 14 days.

Figure 10:
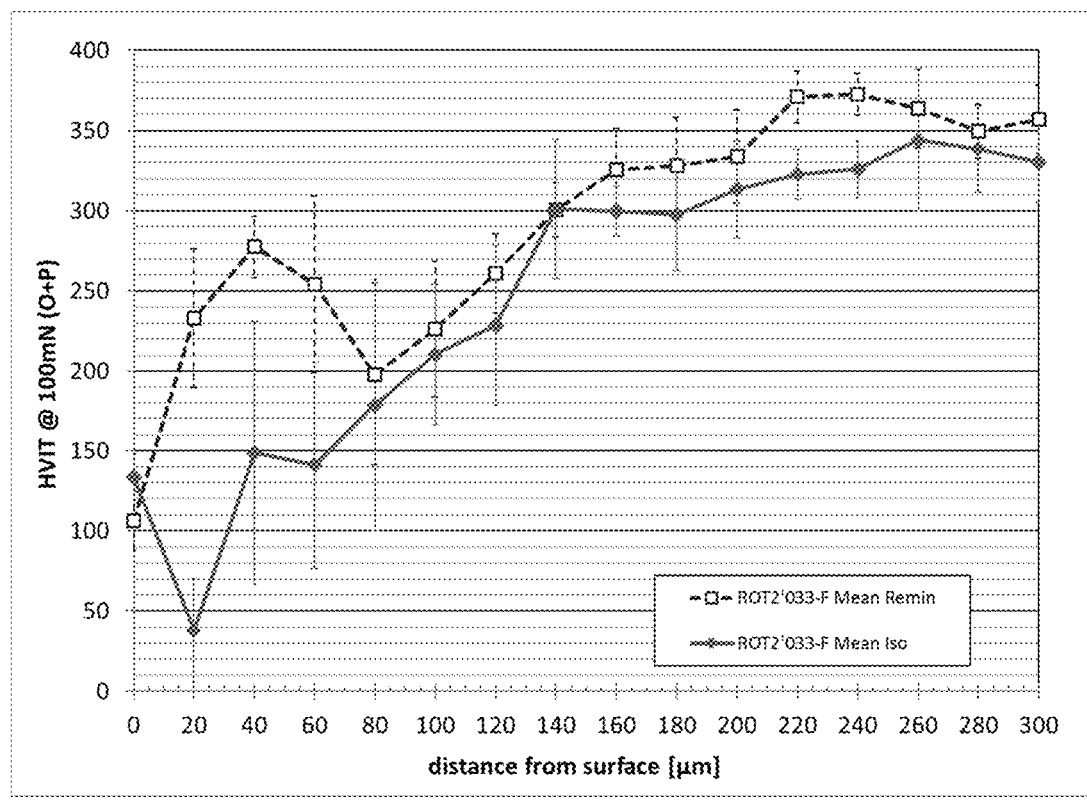
FIG. 10 shows the hardness profile of a tooth region which has been treated with a composition according to the invention (tetrabutylammonium dihydrogen trifluoride, thereafter ethanolic CaF2 nanosol) (dashed curve), compared with an untreated enamel sample (continuous curve).

The hardness profiles in FIG. 10 show a very clear increase in the hardness after the remineralization of the tooth.

Example 10

Remineralization with Ammonium Bifluoride Solution/Calcium Fluoride Nanosol (8.2%)

Remineralization test on an initial lesion by application of a 10% ammonium fluoride solution (5.14 wt.-% fluoride) for 5 minutes and subsequent application of a calcium fluoride nanosol (8.2 wt.-% in water, average particle diameter measured using DLS of approx. 60 nm; obtained from Transparent Materials LLC, Rochester, N.Y. 14615, USA). After the sol had dried up, the teeth were stored in the demineralizing solution for 14 days.

Figure 11:
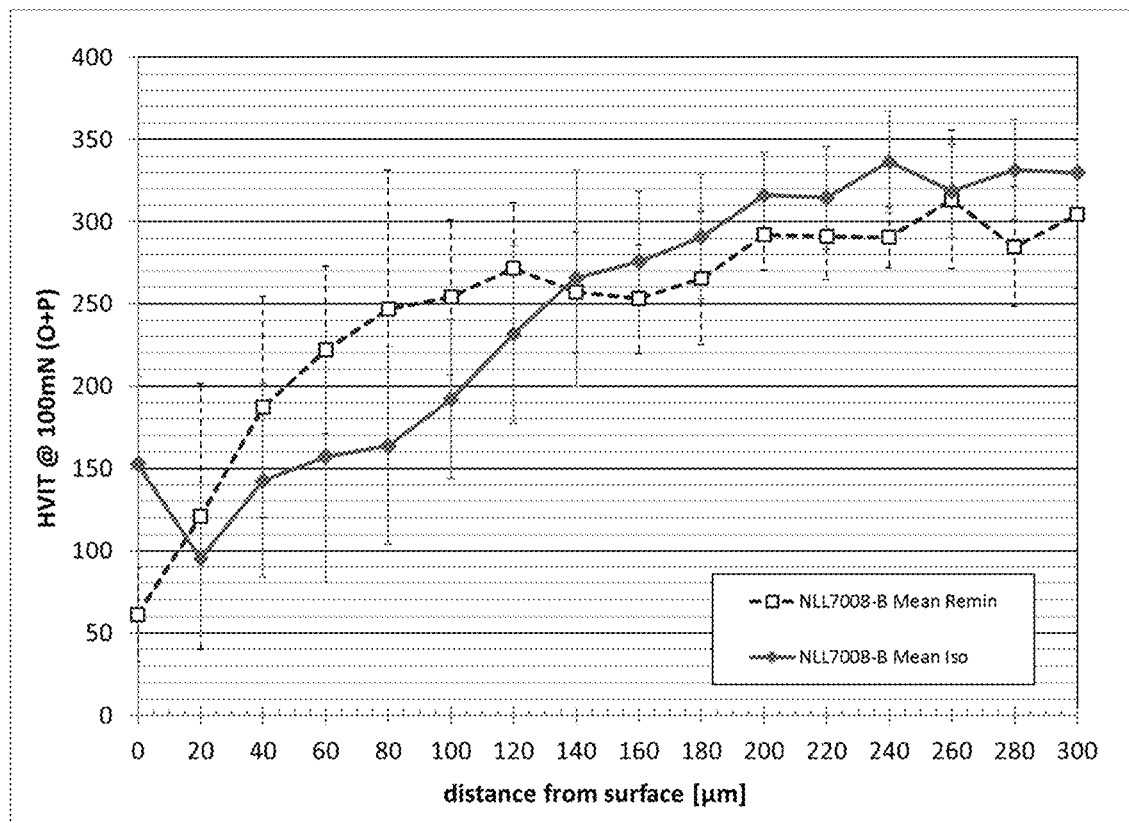
FIG. 11 shows the hardness profile of a tooth region which has been treated with a composition according to the invention (NH4F, thereafter ethanolic CaF2 nanosol) (dashed curve), compared with an untreated enamel sample (continuous curve). The samples were stored in the demineralizing solution for 14 days. The nanoparticles were larger than in FIGS. 6 and 8.

The hardness profiles in FIG. 11 show an increase in the hardness after the remineralization of the tooth.

The invention claimed is:

1. A method of remineralizing teeth comprising
applying a fluoride-containing component to a tooth surface,
applying a calcium-containing component to the tooth surface directly on top of the fluoride-containing component,
wherein the calcium-containing component comprises a nanoparticulate calcium salt suspended in an orally acceptable volatile solvent to form a suspension,
evaporating the solvent to form a solid layer of the nanoparticulate calcium salt,
wherein the fluoride-containing component comprises more than 1500 ppm fluoride (relative to the fluoride anion) in dissolved form and is applied to the tooth before the calcium-containing component,
wherein the fluoride-containing component comprises ammonium fluoride, ammonium bifluoride, potassium fluoride, tetra-n-butylammonium dihydrogen trifluoride or a mixture thereof, and
wherein the calcium-containing component contains no phosphate.

2. The method according to claim 1,
wherein the method is for use in the treatment of initial caries lesions, for caries protection, and for the prevention and/or treatment of dental erosion.

3. The method according to claim 1,
wherein the fluoride-containing component comprises a solution of a fluoride in a solvent.

4. The method according to claim 3,
wherein the solvent comprises water, ethanol, isopropanol, acetone, methanol or a mixture thereof.

5. The method according to claim 1,
wherein the fluoride-containing component comprises more than 5000 ppm fluoride (relative to the fluoride anion) in dissolved form.

6. The method according to claim 1,
wherein the calcium-containing component comprises calcium fluoride, calcium carbonate, calcium sulphate, calcium silicate, calcium oxide or calcium hydroxide.

7. The method according to claim 1,
wherein the nanoparticulate calcium salt has an average particle diameter of <100 nm, measured by dynamic light scattering.

8. The method according to claim 1,
wherein the nanoparticulate calcium salt has an average particle diameter of <30 nm, measured by dynamic light scattering.

9. The method according to claim 1,
wherein the nanoparticulate calcium salt is suspended in a solvent which comprises an alcohol, ester, ether, ketone, alkane, alkene, water or a mixture thereof.

10. The method according to claim 1,
wherein the nanoparticulate calcium salt is suspended in a solvent comprising ethanol, methanol, n-propanol, i-propanol, n-butanol, sec-butanol, isoamyl alcohol, acetone, water, acetonitrile, ethyl acetate, methoxy propanol, dibutyl ether, dioxane, methyl ethyl ketone, heptane, hexane, dimethylformamide, or a mixture thereof.

11. The method according to claim 9,
wherein the nanoparticulate calcium salt is present in an amount of 0.1 wt.-% to 40 wt.-% of the suspension.

12. The method according to claim 9,
wherein the nanoparticulate calcium salt is present in an amount of 1 wt.-% to 30 wt.-% of the suspension.

13. The method according to claim 9,
wherein the nanoparticulate calcium salt is present in an amount of 5 wt.-% to 25 wt.-% of the suspension.

14. The method according to claim 1,
wherein the calcium-containing component is dried after application to the tooth surface.

15. The method according to claim 1,
further comprising etching the tooth with an acid solution before applying the fluoride-containing component.

* * * * *